United States Patent [19]

Bretan, Jr.

[11] Patent Number: 4,920,044

[45] Date of Patent: Apr. 24, 1990

[54] INTRACELLULAR FLUSH SOLUTION FOR PRESERVING ORGANS

[75] Inventor: Peter D. Bretan, Jr., Novato, Calif.

[73] Assignee: The Cleveland Clinic Foundation, Cleveland, Ohio

[21] Appl. No.: 268,809

[22] Filed: Nov. 8, 1988

[51] Int. Cl.$^5$ .............................................. A01N 1/02
[52] U.S. Cl. ........................................... 435/1; 435/2
[58] Field of Search ............................................ 435/1

[56] References Cited

U.S. PATENT DOCUMENTS

| | | | |
|---|---|---|---|
| 4,061,537 | 12/1977 | Seiler et al. ............................... | 435/1 |
| 4,105,798 | 8/1978 | Moore et al. ............................. | 435/1 |
| 4,663,289 | 5/1987 | Veech ....................................... | 435/1 |
| 4,798,824 | 1/1989 | Belzer et al. ............................. | 435/1 |

*Primary Examiner*—Sam Rosen
*Attorney, Agent, or Firm*—Fay, Sharpe, Beall, Fagan, Minnich & McKee

[57] ABSTRACT

The present invention is directed to a new hypersomotic intracellular flush and storage solution for preserving an organ for transplantation. In addition, the present invention is directed to a method for preserving an organ to be transplanted by using the flush solution of the invention. Among the components of the solution are various physiologic salts, mannitol, adenosine, allopurinol and verapamil.

17 Claims, 10 Drawing Sheets

INTRACELLULAR FLUSH SOLUTION FOR PRESERVING ORGANS

BACKGROUND OF THE INVENTION

The present invention relates to a new hyperosmotic intracellular flush and storage solution for preserving an organ for transplantation. In addition, the present invention relates to a method for preserving an organ to be transplanted by using an adenosine-MgSO4, mannitol intracellular flush solution.

While the invention shall be described in connection with the preservation of kidneys, it is understood by those skilled in the art that the intracellular flush and storage solution disclosed herein and the preservation method utilizing the same are applicable to other organs such as the pancreas, the liver, and the heart.

Recently, a great deal of progress has been achieved in the field of organ transplantation through the use of cyclosporine A. Cyclosporine A is a powerful immunosuppressive drug which appears to act mainly on T cells. Through the use of cyclosporine A, a 20% increase in one year allograft survival of kidneys has been noted over that of conventional therapy. However, this advantage appears to be lost with increasing preservation times of the organs to be transplanted (Opelz, G.: *Multicenter Impact of Cyclosporin on Cadaver Kidney Graft Survival,* Prog. Allergy 38: 329-345, 1986). In addition, there is increasing evidence that moderate ischemic injury based upon unsatisfied metabolic oxygen demand may predispose renal allografts to severe rejection and diminished survival (Keller, H., Fischer, G., Kirste, G., Wilms, H.: *ATN Influence on Renal Transplant Function,* Transpl. Proc. (in press) 1989). Thus, in today's cyclosporine era, better preservation techniques are essential for optimal allograft survival, not just to diminish the detrimental effects of prolonged preservation times, but also to prevent the occurrence of delayed graft function which is associated with further graft loss using cyclosporine prior to the complete resolution of post renal transplant acute tubular necrosis (Bia, M. J., Tyler, K. A.: *Effect of Cyclosporine on Renaischemic Injury,* Transplantation, 43:800-804, 1987).

In this regard, a great deal of research progress has been made over the years in understanding cellular mechanisms, as well as developing new preservation techniques for keeping kidneys and other organs viable not only during cold storage, but also after revascularization and reperfusion of these organs. Early investigators were mainly interested in studying physiologic characteristics of isolated organs. Their methods allowed only very short observation periods before the organs suffered irreversible ischemic damage due to the lack of blood supply. However, in 1938, Carrel and Lindbergh contributed substantially to the knowledge in organ preservation by showing that kidneys could be kept viable extracorporeally for a limited time by using a special blood perfusion apparatus (Carrel, A. and Lindbergh, C. A.: *The Culture of Organs,* New York, Paul B. Hoeber, Inc., 1938). Later, profound hypothermia (i.e. a much lower than normal temperature) was found to prolong the period in which tissue could tolerate ischemia.

Moreover, successful cadaver kidney transplantation in the early 1960's greatly stimulated further work in the field of renal preservation. In 1963, Humphries and co-workers reimplanted dog kidneys after 24 hours of extracorporeal hypothermic perfusion with diluted serum or plasma (Humphries A. L., et al.: *Successful Reimplantation of Canine Kidney After Twenty Four Hour Storage,* Surgery, 54:136, 1963). Belzer and colleagues, in 1967, achieved a very significant breakthrough by preserving dog kidneys for as long as 72 hours using hypothermic pulsatile perfusion with cryoprecipitated plasma (Belzer, F. O., Ashby, B. S., Dunphz, J. E.: *Twenty Four Hour and Seventy Two Hour Preservation of Canine Kidneys,* Lancet 2: 536, 1967). This was very quickly followed by consistently successful human cadaver kidney preservation using Belzer's method. Subsequently, Johnson, et al. transplanted canine kidneys preserved with pulsatile perfusion but employing plasma protein fraction (PTF) as the perfusate (Johnson, R. W. G., et al.: *Evaluation of a New Perfusion Solution for Kidney Preservation,* Transplantation, 13:270, 1972), while Claes and associates introduced 4.5% human albumin solution as a kidney preservation perfusate (Claes, G., et al.: *Albumin as Perfusate in Continuous Perfusion for Renal Preservation,* Fourth International Transplant Conference, New York, Grune and Stratton, p. 46, 1972). In 1969, Collins and colleagues had further simplified the preservation technique by showing that ample storage of dog kidneys in ice slush following immediate initial flushing with an intracellular electrolyte solution was successful in preserving the kidney for as long as 30 hours (Collins, G. M., Bravo-Sugarma, M., and Terasaki, P.: *Kidney Preservation for Transplantation,* Lancet, 2:1219, 1969).

Today, both simple cold storage and continuous pulsatile perfusion are used in clinical renal transplantation, either separately or in combination. Simple cold storage is used more extensively because it is generally accepted that a human cadaver kidney can be safely preserved by the simple cold storage method when the kidney has sustained only minimal ischemia and can be implanted within 40 hours. Otherwise, hypothermic pulsatile perfusion has been recommended.

Simple cold storage combines the hypothermic and flush solution effects to decrease metabolic activity and prevent subsequent cell swelling and acidosis. Simple cold storage is accomplished by rapidly cooling the kidney immediately after harvesting by flushing the renal vasculature with chilled electrolyte solution and then placing the kidney in ice slush. The core temperature is kept between 0° and 4° C. by placing the sterile sealed kidney container in ice, where it is kept until the cadaver transplant procedure can be performed. This method of preservation is also employed for most extracorporeal renal operations.

Although simple cold storage methods have offered consistently successful preservation of kidney viability up to 48 hours (Halasz, N. A., Collins, G. M.: *Forty-Eight Hour Kidney Preservation: A Comparison of Flushing and Ice Storage with Perfusion,* Arch. Surg. 111:175-177, 1976), this time period becomes more critical if the cadaver donor was poorly prepared prior to donor nephrectomy or if the kidney has sustained a period of warm ischemia. In these situations, hypothermic pulsatile perfusion after renal flushing with a chilled electrolyte solution is the preferred method of renal preservation. An advantage of this method is a longer safe preservation period, in some cases as long as 72 hours. Most transplantation centers are employing human cadaver kidneys that have been preserved for longer periods than in the past, due to an increase in regional and national organ sharing. These kidneys can be readily transported in a portable pulsatile renal preservation unit. Compared to simple hypothermia, pulsatile perfusion is technically more complex and more costly (Alijani, M. R., et al.: *Single-donor Cold Storage vs. Machine Perfusion in Cadaver Kidney Preservation*, Transplant 40:659–661 1985), however, it does seem to offer more reliable preservation in the 48 to 72 hour range, thus this type of preservation is often used for questionably viable kidneys obtained from inadequately prepared cadaveric donors or rare AB kidneys, which may travel through several centers prior to matching with an appropriate recipient.

The ability to successfully preserve the kidney for as long as 72 hours has been of immense benefit to cadaver renal transplantation. This has provided sufficient time for both histocompatibility testing of the donor and sensitive cross match testing for preformed cytotoxic antibodies in the recipient or for organ sharing between transplant centers. However, notwithstanding the above, improved preservation techniques, including enhanced intercellular flush solutions, are needed not only to extend the preservation period, but also to improve the quality of the organs transplanted.

To understand existing renal preservation techniques and the rationale for potentially new developments, one must first understand what occurs at the cell level during periharvest warm ischemia, subsequent hypothermic storage (cold ischemia) and reperfusion, such as diminished metabolic activity, as well as cessation of cell membrane function which leads to cell swelling and acidosis. Concurrent with this there is a continued loss of intracellular energy stores which subsequently generates toxic free radicals, contributing to further endothelial damage or "reperfusion" injury after revascularization upon transplantation.

More particularly, as a result of the deprivation of circulation, and thus oxygen (i.e. ischemia), during transplantation, the sodium pump of the renal cells, which normally maintains the intracellular composition of the renal cells high in potassium, magnesium, and phosphate and low in sodium and chloride, ceases to function due to the lack of energy, resulting in an inflow of sodium and chloride into the cells, and an outflow of potassium and to a lesser extent magnesium from the cells (Sacks, S. A., Petritsch, P. H., Kaufman, J. J.: *Canine Kidney Preservation Using a New Perfusate*, The Lancet, May 12, 1973; 1024–1028). The result of these rapid changes in ion distribution in the ischemic cell is a net gain, not merely an exchange, of intracellular ions (sodium and chloride) followed passively by water (Leaf, A. *Ann. N.Y. Acad. Sci.*, 72, 396, 1959) and a profound loss of potassium and to a lesser extent magnesium (Keeler, R., Swinney, J., Taylor, R. M. R., Uldall, P. R., *Br.J. Urol.*, 38, 653, 1966). Moreover, the remaining non-diffusible intracellular molecules (with electronegative charge) exert Donnan and osmotic forces, resulting in the further movement of water into the cell (Leaf, A., *Am. J. Med.*, 40, 291, 1970). The morphological consequence of these changes in ion and water distribution of the renal cells is characterized by "cellular swelling" which impedes the flow of blood through the kidneys. Red blood cells have been shown to impact in the swollen glomerular capillary bed after macrocirculation has been reestablished to kidneys subjected to ischaemia (Summers, W. K., Jamison R. L., *Lab. Invest.* 25, 635, 1971) thereby markedly reducing the efferent flow to the peritubular capillaries. The ischemic insult to the renal tubular cell may thus be perpetuated even after the macrocirculation has been reestablished (Sacks, supra.).

Moreover, there is increasing evidence that much of the damage resulting from a period of warm or cold ischemia in many organs, including the kidneys, is produced by the continued loss of intracellular energy stores which subsequently generates toxic free radicals which damage cell membranes of the endothelial cells which line the fine microcirculation of the kidney upon transplantation (i.e. reperfusion injury). The mechanism involved in the free radical generation in the ischemic tissues at reperfusion is now thought to be known. Briefly, the high energy phosphate compounds are broken down stepwise (ATP - ADP - AMP) with the onset of ischemia, resulting in the accumulation of hypoxanthine, the concentration of which increases progressively during the period of ischemia. There is also rapid proteolytic conversion of xanthine dehydrogenase to xanthine oxidase during the period of ischemia. Consequently, both activated enzyme (xanthine oxidase) and its oxidizable substrate (hypoxanthine) are present in excess. At the moment of reperfusion, the reducible substrate, molecular oxygen, is supplied suddenly and in excess, leading to a burst of superoxide radical production. Both superoxide anions and their toxic descendants, including hydroxyl radical, can cause tissue injury (Hoshino, T.; Maley, W.; Bulkey, G.; and Williams, G.: *Ablation of Free Radical-Mediated Reperfusion Injury for the Salvage of Kidneys taken from Non-heartbeating Donors*, Transplantation, Vol. 45, 284–289). Normally, the cytochrome oxidase complex present in the kidneys and other organs can supply enzymes such as supraoxide dismutase and catalase (SOD+CAT) to scavenge these free radicals and rid the cell of these toxins by further degradation. However, with ischemia these are not sufficient to prevent further injury after reperfusion.

In an attempt to deactivate the harmful $O_2^-$ and $OH^-$ free radicals, mannitol (Pavlock, G. S., et al.: *Effects of Mannitol and Chlorpromazine on Pretreatment of Rabbits on Kidney Mitochondria Following In Vivo Ischemia and Reflow*, Life Sci. 29: 2667–72, 1981), DMSO (Hansson, R., et al.: *Effect of Xanthine Oxidase Inhibition of Renal Circulation After Ischemia*, Transplant. Proc. 14:51–8, 1982), and L-methionine (Hansson, supra) have been added with only a limited degree of success. Moreover, there has also been much controversy about the role of calcium in ischemic nephrotoxicity. It is postulated that calcium activates various calcium dependent phospholipases which start a cascade of reactions which amplify the destructive effects of ischemia. The cascade responsible for the cell membrane degradation, may be inhibited somewhat by calmodulin inhibitors, calcium entry blockers (CEBs), or Chlorpromazine (Frega, W. S., et al.: *Ischemic Renal Injury*, Kidney Int. 10:517–25, 1976) (Pavlock, G. S., et al.: *Effects of Mannitol and Chlorpromazine Pretreatment of Rabbits on Kidney Mitochondria Following In Vivo Ischemia and Reflow*, Life Sci. 29:1667–72, 1981). Thus, it is not only important to understand what is going on in the kidney during cold storage, but also to reassess what occurs in the immediate reperfusion period post renal transplant. In order to counteract the above pathologic processes which occur at the cell level during warm ischemia, subsequent hypothermia storage and reperfusion, cold storage (i.e. hypothermia) and various electrolyte flushing solutions have been used to extend the preservation times of the kidneys to be transplanted. The main function of hypothermia (4°–8° C.) is to slow metabolic activity and intracellular respiration by a factor of 10–20, extending the one hour normothermic (37° C.) limit to 13 hours of cold. By maintaining the kidney in a cold state, the metabolic needs of the kidney are kept to a minimum. Thus, the objective of cold storage is to bring the kidney as rapidly as possible to a temperature close to its freezing point without subjecting it to shock and to maintain the kidney at this low temperature until just prior to transplantation, when its temperature is raised to a level close to normal body temperature.

In order to extend organ preservation by cold storage (hypothermia), various electrolyte flushing solutions have been developed over the years to be utilized in combination with hypothermia. Initially, the principle aims were to achieve rapid cooling and to wash out the blood with its particulate compounds, coagulation factors, and isoaggultinins (Collins, G. M.: *Current Status of Renal Preservation by Simple Flushing and Hypothermic Storage*, Renal Preservation, Chapter 15, 224–243). Little attention was paid to the precise composition of these solutions which were chosen on the whole from those readily available to clinical use and were thus basically of extracellular composition. (Collins, supra at 226).

In this regard, Ringer's lactate and isotonic saline solutions were determined to be fairly good extracellular flushing solutions that allowed safe renal preservation for short periods of time, i.e. up to four hours. Thus, extracellular solutions may be used in the living renal donor transplant setting for short periods of preservation time, however, longer periods are not advised. For example, the present inventors have observed severe histologic ischemic damage and subsequent nonfunction in dog kidneys preserved for five hours by cold storage after flushing with Ringer's lactate solution.

However, notwithstanding the above, it was discovered that intracellular electrolyte solutions, such as the intracellular electrolyte solution developed by Collins and associates (Collins, G. M., Bravo-Sugerma, M., and Terasaki, P.: *Kidney Preservation for transplantation*, Lancet 2:1219, 1969) offer several advantages for simple cold storage in comparison with other recently developed intracellular flush solutions. Table 1 below shows the ingredients of the Collins solution (solution C2) most commonly used today in comparison with other recently developed intracellular flush solutions.

TABLE 1

COMPOSITION OF DIFFERENT INTRACELLULAR RENAL FLUSH SOLUTIONS (g/l)

|  | COLLINS-2 FLUSH | SACKS-2 FLUSH | BELZER PERFUSATE | UW-1 FLUSH |
|---|---|---|---|---|
| $KH_2PO_4$ | 2.0 | 4.16 | 3.4 | 3.4 |
| $K_2HPO_4$ $3H_2O$ | 9.70 | 9.70 | — | — |
| KCl | 1.12 | — | — | — |
| $KHCO_3$ | — | 2.30 | — | — |
| Mannitol | — | 37.5 | — | — |
| Glucose | 25 | — | 1.5 | — |
| $MgSO_4 7H_2O$ | 7.38 | — | 8 | 1.2 |
| $MgCl_2$ | — | (2 meq/ml) | — | — |
| Adenosine | — | — | 1.3 | 1.34 |
| Sodium Glutathione | — | — | 17.5 | 0.92 |
| Albumin | — | — | 5.3 | — |
| $NaHCO_3$ | 0.84 | 1.26 | — | — |
| Allopurinol | — | — | 0.113 | 0.113 |
| Verapamil | — | — | — | — |
| K+-Lactobionate | — | — | — | 39.8 |

TABLE 1-continued

COMPOSITION OF DIFFERENT INTRACELLULAR RENAL FLUSH SOLUTIONS (g/l)

|  | COLLINS-2 FLUSH | SACKS-2 FLUSH | BELZER PERFUSATE | UW-1 FLUSH |
|---|---|---|---|---|
| Raffinose | — | — | — | 17.8 |
| Hydroxyethyl Starch | — | — | — | 50 |
| Osmolality (mOsm/kg) | 320 | 430 | 300 | 320–330 |
| pH | 7.00 | 7.00 | 7.10 | 7.40 |

In addition, a number of "modified" Collins' solutions have been produced in an attempt to improve the preservation properties (i.e. duration and quality of kidney storage) of the flush solution for simple cold storage. In this regard, Euro-collins solution is similar to Collins' solution except it does not contain magnesium. Despite this, multiple studies have shown equivalent preservation using both types of Collins' flush solutions during simple hypothermic storage. The exact mechanism of action and the significance of the ionic composition of the intracellular flushing solution have been disputed. Belzer and Downes performed interesting laboratory experiments comparing Collins' solution and hyperosmolar Ringer's lactate solution, and concluded that cellular potassium loss during cold storage is not as critical to subsequent renal function as is the prevention of water gain (Belzer, F. O., Downes, G. L.: *Organ Preservation for Transplantation*, Boston, Little, Brown, 1974). These authors also suggested that the osmotic effect of a high glucose content in Collins' solution was more important than were the high potassium and magnesium concentrations. Nevertheless, it is well accepted that these phosphate buffer solutions are quite effective in preventing cell swelling and acidosis during simple hypothermia storage as previously discussed.

Furthermore, Sacks and his associates developed a number of flush solutions ($S_1$ and $S_2$) which reportedly improved transplantation results after storage of kidneys up to 72 hours in a modified perfusion fluid with high intracellular ion concentration and osmotic pressure. (Sacks, S. A., Petritsh, P. H., Kaufman, J. J.: Lancet 1:1024, 1973). Table 1 illustrates the composition of Collins' C-2 solution in comparison with Sacks' S-2. The most significant changes were higher K+ and lower Na+ concentrations and the substitution of 37.5 g/liter of mannitol for glucose as t he osmotic active substance thereby increasing the osmolarity from 310 to 430 in Osmol/liter. However, there are many studies that show that the Sacks' solutions exhibit inferior preservation properties when compared to Collins' C-2 solution (Collins, G. M.: *Current Status of Renal Preservation by Simple Flushing and Hypothermic Storage*, Renal preservation, edited by M. Marberger and K. Dreikorn, Williams & Wilkins, Baltimore, Chapter 15, p. 224–236, 1983) as well as failure to achieve 48 hours of safe preservation adequately (Chatterjee, S. N., Berne, T. V.: *Failure of 48 Hours of Cold Storage of Canine Kidneys Using Sacks Solution*, Transpl. 19:441–442, 1975). The basic difference that may account for this is the lack of adenosine and the low content of magnesium in the S-2 solution; as well as, the substitution of mannitol for glucose as the osmotic active substance. Mannitol may have a detrimental influence on the cells by causing structural changes, it is probably only temporary (Dahlager, J. I., and Bilde, T.:

*The Integrity of Tubular Cell Function After Preservation in Collins' or Sacks' Solution*, Transpl. 21: 365-369, 1976). Moreover, the greater hyperosmolarity of the Sacks' solution (410-430 mOsm/kg) may greatly increase the tendency of mannitol and magnesium phosphate to precipitate out from solution within the kidney during cold storage (Collins, supra).

Moreover, since 1976, there have been numerous animal studies supporting the use of protective additives such as ATP-Mg $Cl_2$ (Siegel, N. J., et al.: *Enhanced Recovery of Renal ATP with Post Ischemic Infusion of ATP-Mg $Cl_2$ Determined by 31P-NMR*, Am. J. Physiol. 245:F530-534, 1983); (Stromski, M. E., et al.: *Postischemic ATP-Mg $Cl_2$ Provides Percursors for Resynthesis of Cellular ATP in Rats*, Am. J. Physiol. 250:F834-F837, 1986); and, (Sumpio, B. E., et al.: *Accelerated Functional Recovery of Isolated Rat Kidney with ATP-Mg $Cl_2$ After Warm Ischemia*, Am. J. Physiol. 247:R1047-R1053, 1984), AMP-Mg $Cl_2$ (Stromski, M. E., et al.: *Postischemic ATP-Mg $Cl_2$ Provides Percursors for Resynthesis of Cellular ATP in Rats*, Am. J. Physiol. 250:F834-F837, 1986) or inosine in flush or perfusate solutions. These additives are associated with improvement in post reperfusion microcirculation and subsequent regeneration of intracellular ATP (Stromski, M. E., et al.: *Chemical and Functional Correlates of Post Ischemic Renal ATP Levels*, Proc. Natl. Acad. Sci. 83:6142-6145, 1986). It is postulated that these additives do not actually "recharge" the intracellular energy stores of renal cells, but they either slow the degradation of energy stores or supply substrate during the immediate re-perfusion period enabling prevention of cell swelling of intrarenal vascular endothelia cells, thus minimizing other aspects of the "reperfusion injury". Since hypothermia slows the ischemic induced degradation of ATP (Stromski, M. E., et al.: *Chemical and Functional Correlates of Post Ischemic Renal ATP Levels*, Proc. Natl. Acad. Sci. 83:6142-6145, 1986) and adenosine to hypoxanthine by a factor of 20, by adding ATP-Mg $Cl_2$ or inosine this process may be slowed even more, generating even less hypoxanthine. With less hypoxanthine, less $O_2^-$ is generated during re-perfusion and the cytochrome oxidase complex can now deal more efficiently with degradation of free radicals.

Furthermore, Belzer and his associates have recently developed a number of perfusates which demonstrate enhanced preservation properties. The improved post transplant microcirculation that was first noted in clinical renal transplant settings using Belzer perfusate (Belzer, F. O., et al.: *A New Perfusate for Kidney Preservation*, Transpl. Proc. 16:161-163, 1984) (containing ATP-Mg $Cl_2$) in 1984 has been reproduced by many centers and has been associated with a significantly higher immediate function rate compared to perfusates containing silicate gel (Henry, M. L., Sommer, B. G., Ferguson, R. M.: *Improved Immediate Function of Renal Allographs with Belzer Perfusate*, Proc. American Society of Transplant Physicians, p. 70, 1987). However, the Belzer ATP-Mg $Cl_2$ perfusate has not been used for simple storage, limiting its widespread use and value (Arch. Surg. 122: 790-794, 1987).

In addition, good results have also been recently reported through the use of a UW-1 solution produced by the University of Wisconsin (Wahlberg, J. A., Love, R., Landegaard, L., et al.: *72 hour Preservation of the Canine Pancreas*, Transpl. 43:5-8, 1987); and (Ploeg, R. J., Goossens, D., McAnulty, et al.: *Successful 72 Hour Storage of Dog Kidneys with UW Solution* [submitted for publication]). The overall composition of UW-1 solution in comparison to the Collins' C-2, Sacks' S-2, and Belzer's Perfusate is set forth in Table 1. However, concerns over the possibility of allergic reaction from the high concentration of hydroxyethyl starch (50 gl/l) and the lack of FDA approval have slowed widespread availability and usage of the UW-1 solution.

As a result of the above indicated difficulties, the present inventors have conducted a great deal of experimental research in an attempt to produce a simple hypothermic intracellular flush and storage solution which enhances organ, particularly kidney, preservation both by diminution of reperfusion injury and by decreasing the loss of intracellular high energy metabolites that are necessary for viability. The present invention is the result of such experimental research.

SUMMARY OF THE INVENTION

In one aspect, the present invention relates to a new hyperosmotic intracellular flush and storage solution for preserving an organ for transplantation comprising between about 1.54 and 2.56 grams per liter of $KH_2PO_4$; between about 7.38 and 12.2 grams per liter of $K_2HPO_4$; between about 0.84 and 1.40 grams per liter of KCl; between about 0.63 and 1.05 grams per liter of $NaHCO_3$; between about 0 and 2.87 grams per liter of $KHCO_3$; between about 20 and 37 grams per liter of mannitol; between about 0 and 4.62 grams per liter of $MgSO_4$; between 0 and 0.4 meq/ml of $MgCl_2$; between about 0.75 and 1.25 grams per liter of adenosine; between about 0 and 0.125 grams per liter of allopurinol; and, between about 0 and 1.0 grams per liter of verapamil.

In another aspect, the present invention concerns an intracellular flush solution for preserving an organ for transplantation comprising about 2.05 grams per liter $KH_2PO_4$; about 9.7 grams per liter $K_2HPO_4$; about 1.12 grams per liter KCl; about 0.84 grams per liter $NaHCO_3$; about 25.0 grams per liter mannitol; about 3.7 grams per liter $MgSO_4$; and about 1.0 grams per liter adenosine.

In an additional aspect of the invention, the present invention concerns an intracellular flush solution for preserving an organ for transplantation comprising about 2.05 grams per liter $KH_2PO_4$; about 9.7 grams per liter $K_2HPO_4$; about 1.12 grams per liter KCl; about 0.84 grams per liter $NaHCO_3$; about 2.3 grams per liter $KHCO_3$; about 25.0 grams per liter mannitol; about 3.7 grams per liter $MgSO_4$; about 1.0 grams per liter adenosine; about 0.1 grams per liter allopurinol; and, about 0.007 grams per liter verapamil.

In a further aspect of the invention, the present invention relates to a method for preserving an organ for transplantation comprising flushing the organ to be transplanted with an intracellular flush solution containing between about 1.54 and 2.56 grams per liter of $KH_2PO_4$; between about 7.38 and 12.2 grams per liter of $K_2HPO_4$; between about 0.84 and 1.40 grams per liter of KCl; between about 0.63 and 1.05 grams per liter of $NaHCO_3$; between about 0 and 2.87 grams per liter of $KHCO_3$; between about 20 and 37 grams per liter of mannitol; between about 2.77 and 4.62 grams per liter of $MgSO_4$; between 0 and 0.4 meq/ml of $MgCl_2$; between about 0.75 and 1.25 grams per liter of adenosine; between about 0 and 0.125 grams per liter of allopurinol; and, between about 0 and 1.0 grams per liter of verapamil.

In still another aspect of the invention, the present invention concerns a method for preserving an organ for transplantation comprising flushing the organ to be transplanted with an intracellular flush solution comprising about 2.05 grams per liter $KH_2PO_4$; about 9.7 grams per liter $K_2HPO_4$; about 1.12 grams per liter KCl; about 0.84 grams per liter $NaHCO_3$; about 25.0 grams per liter mannitol; about 3.7 grams per liter $MgSO_4$; and about 1.0 grams per liter adenosine.

In a still further aspect of the invention, the present invention relates to a method for preserving an organ for transplantation comprising flushing the organ to be transplanted with an intracellular flush solution comprising about 2.05 grams per liter $KH_2PO_4$; about 9.7 grams per liter $K_2HPO_4$; about 1.12 grams per liter KCl; about 0.84 grams per liter $NaHCO_3$; about 2.3 grams per liter $KHCO_3$; about 25.0 grams per liter mannitol; about 3.7 grams per liter $MgSO_4$; about 1.0 grams per liter adenosine; about 0.1 grams per liter allopurinol; and, about 0.007 grams per liter verapamil.

DESCRIPTION OF THE DRAWINGS

The following is a brief description of the drawings which are presented for the purpose of illustrating the invention and not for the purpose of limiting same.

DETAILED DESCRIPTION OF THE INVENTION

Figure 1:
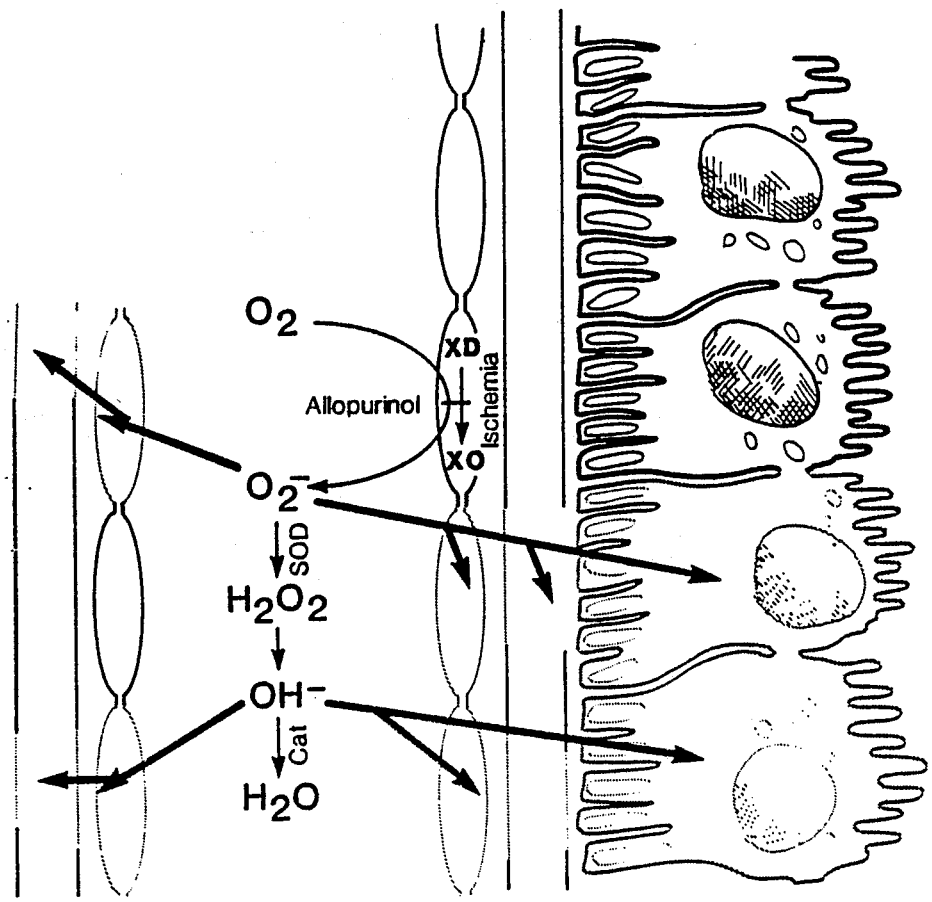
FIG. 1 is a schematic diagram illustrating reperfusion injury after transplant revascularization.

The present invention is directed to new hypersomotic intracellular flush and storage solution for preserving an organ, such as in kidney, for transplantation. The individual components of the present invention are all non toxic and have been found to be stable for storage indefinitely (i.e. greater than 4 months). While some of the components of the present invention are similar to those of other known intracellular flush solutions such as Collins-2 Flush, (a product of Baxter-Travenol, Deerfield, Ill.) Sacks-2 Flush, Belzer Perfusate, and UW-1 Flush (See Table 1), the intracellular flush solution of the present invention was specifically designed to minimize adenine nucleotide (AN) catabolism and post-preservation renal reperfusion injury. As a result of these improved characteristics, the flush solution of the present invention has been found to be more efficacious than previously known intracellular flush solutions in extending organ viability during simple cold storage.

More particularly, the present invention relates to an improved flush and simple storage solution which combines the salient features of Belzer's ATP-$MgCl_2$ perfusate and the simplicity of most commonly used Collins' C-2 flush solutions. In this regard, mannitol has been substituted in place of dextrose in Collins' C-2 solution because the present inventors have found that mannitol, when utilized in the specific concentrations, and in combination with the particular components of the present invention, enhances organ preservation by reducing the reperfusion injury not alleviated by the Collins C-2 solutions. Since mannitol has multiple modes of action for organ preservation, i.e. for example mannitol is an effective free radical scavenger for $OH^-$ (Pavlock G. S., et al.: *Effects of Mannitol and Chloropromazine Pretreatment of Rabbits on Kidney Mitochondria Following In Vivo Ischemia and Reflow,* Life Sci, 29:2667–72, 1981), a detoxifier, (Palafox N. A., Luis G. J., Alexander Z., et al.: *Successful Treatment of Ciguatera Fish Poisoning with Intravenous Mannitol,* JAMA 259:2740–2742, 1988) and an indispensable constituent of intraoperative hydration protocols for the prevention of acute renal failure after renal cadaveric transplantation (Valenberg P. L., Hoitsma A. J., Tiggeler R. G., et al.: *Mannitol as an Indispensable Constituent of an Intra Operative Hydration Protocol for the Prevention of Acute Renal Failure After Renal Cadaveric Transplantation,* Transpl. 44:784–788, 1987) its specific mode of operation is not clearly known at this time. On the other hand, dextrose (D-glucose), which is currently used for its hyperosmolar effect in the Collins' C-2 flush solution, has been recently shown to exacerbate acute renal ischemic damage in dogs (Moursi, M, Rising C. L., et al.: *Dextrose Administration Exacerbates Acute Renal Ischemic Damage in Anesthetized Dogs,* Arch. Surg. 122:790–794, 1987). Thus, as a result of the enhanced properties demonstrated by mannitol, and the harmful effects produced by dextrose, mannitol was substituted for dextrose in the present invention.

In addition, adenosine and magnesium were also added to the present invention in order to improve the preservation properties of the flush solution. In this regard, both adenosine (Stromski M. E. et al.: *Post Ischemic ATP-Mg Cl$_2$ Provides Precursors for Resynthesis of Cellular ATP in Rats,* Am. J. Physiol. 250: F834–F837, 1986; and, Belzer O. F., Sollinger H. W., Glass N. R., et al.: *Beneficial Effects of Adenosine and Phosphate in Kidney Preservation,* Transpl. 36:633, 1983) and magnesium (Collins, G. M.: *Current Status of Renal Preservation by Simple Flushing and Hypothermic Storage,* IN Renal Preservation, edited by M. Marberger and K. Dreikorn, Williams & Wilkins, Baltimore 1983, Chapter 15, p224–236; and, Collins, G. M., Halasz, N. A.: *48 Hour Ice Storage of Kidneys—Importance of Citation Content,* Surg. 79:432–435, 1976) have been shown to improve post reperfusion microcirculation and to enhance the maintenance and regeneration of intracellular ATP and AN. Moreover, magnesium also exhibits a vasodilator effect and acts as a metabolic inhibitor (Collins, supra).

As the result of the substitution of multiple amounts of mannitol for dextrose in Collins' C-2 solution, as well as, the addition of various amounts of adenosine and magnesium, the overall composition of the present invention exhibits greatly improved organ preservation properties over other known flush solutions including Collins' C-2 solution. These enhanced properties have been verified, as more clearly demonstrated below in Example 1, by recent research viability techniques, such as phosphorus-31 magnetic resonance spectroscopy ($^{31}$P-MRS), electron microscopy (EM) and high performance liquid chromatograph (HPLC).

The adenosine-MgSO$_4$, mannitol intracellular flush solution of the present invention can be prepared according to the constituent ranges set forth in Table 2 below.

TABLE 2

COMPOSITION OF THE DIFFERENT INTRACELLULAR FLUSH SOLUTIONS OF THE PRESENT INVENTION (g/l)

|  | PB-2 | PB-3 | RANGES |
|---|---|---|---|
| KH$_2$PO$_4$ | 2.05 | 2.05 | 1.54–2.56 |
| K$_2$HPO$_4$3H$_2$O | 9.70 | 9.70 | 7.38–12.2 |
| KCl | 1.12 | 1.12 | 0.84–1.40 |
| NaHCO$_3$ | 0.84 | 0.84 | 0.63–1.05 |
| KHCO$_3$ | — | 2.30 | 0–2.87 |
| Mannitol | 25.0 | 25.0 | 20–37 |
| MgSO$_4$ | 3.7 | 3.7 | 0.0–4.62 |
| or | or | or |  |
| MgCL$_2$ | 0.3 | 0.3 | 0.0–0.4 meq/ml |
| Adenosine | 1.0 | 1.0 | 0.75–1.25 |
| Allopurinol | — | 0.100 | 0–0.125 |
| Verapamil | — | 0.007 | 0–1.0 |
| Osmolality (osm/kg) | 340 | 340 | 255–425 |
| pH | 7.25 | 7.30–7.40 | 7.20–7.50 |

While the various components of the particular embodiments of the present invention (i.e. PB-2 and PB-3 solutions) can be mixed in a liter of distilled water to produce the overall composition, in practice, the specified amounts of mannitol, magnesium, adenosine, KHCO$_3$, allopurinol and/or verapamil are added to a liter of Collins' C-2 solution (Baxter-Travenol). The specific components of Collins' C-2 solution are set forth in Table 1. When Collins' C-2 solution is commercially purchased, the solution is devoid of dextrose and magnesium. These two components are normally added later prior to use. Thus, most commercially available Collins' C-2 solutions provide an excellent base for the present invention.

Utilizing commercially available Collins' C-2 solution devoid of dextrose and magnesium as a base (i.e. modified Collins' C-2 solution), the PB-2 embodiment of the present invention is prepared by mixing together adenosine, MgSO$_4$ and mannitol with one liter of modified Collins' C-2 solution so that the concentrations of KH$_2$PO$_4$, K$_2$HPO$_4$, KCl, NaHCO$_3$, mannitol, MgSO$_4$, and adenosine may assume respectively the concentration values set forth in Table 2. The resulting PB-2 solution exhibits an osmolality of 340 mOsm/kg and a pH of 7.25.

Moreover, the present invention is also directed to enhanced embodiments of the adenosine-MgSO$_4$, mannitol intracellular flush solutions (such as PB-2) described above. Recent evidence strongly supports the use of other additives, such as enzyme inhibitors, free radical scavengers, buffers and calcium entry blockers (CEB), for enhanced organ preservation. For example, the use of allopurinol (Hoshino T., Maley W. R., Bulkley G. B., Williams G. M.: *Ablation of Free Radical-mediated Reperfusion Injury for the Salvage of Kidneys Taken from Non-heart Beating Donors—a Quantitative Evaluation of the Proportion of Injury Caused by Reperfusion Following Periods of Warm, Cold and Combined Ischemia,* Transpl. 45:284–289, 1988) to slow the generation of oxygen free radicals at reperfusion has been successful, as well as the use of histidine for a higher pH buffering capacity (Busza A. C., Fuller B. J., et al.: *Improved Maintenance of Tissue Phosphorus Metabolites and Control of Tissue pH as Demonstrated by $^{31}$p-MRS in Rat Livers Flushed—Stored at 4° C. Using a Histidine-buffered Citrate Solution,* Proc. Soc. Mag. Reson. Med; p465, San Francisco, 1988). 2'-deoxycoformycin has been used to increase the residual AN pool by inhibition of 5'-nucleotidase, the enzyme responsible for the break down of high energy ANs to hypoxanthine during ischemia (Van Waande A., Stromiski M. E., Thulin K. M., et al.: *Protection of Kidney Against Ischemic Injury by Inhibition of 5'-Nucleotidase,* Proc. Soc. Mag. Reson. Med; p628, San Francisco, 1988). Similarly, the use of Calcium Entry Blockers (CEB) for both donor pretreatment (Ishigami M., Magnusson M., Stowe N., Straffon R.: *The Salutary Effect of Verapamil and Propranolol in Ischemically Damaged Kidneys,* Tranpl. Proc. 16(1), Feb, 1984; and Korb S. M., Albornoz W., Brem A.: *Verapamil Pretreatment of Hemodynamically Unstable Donors Prevents Acute Tubular Necrosis Post-transplant,* Transpl. Proc. (in press 1989); Proc. for the Int. Congress Transpl., Sydney Australia, p.225, 1988) and as a cold flush additive (Neumayer H. H., Schreiber M., Wagner K.: *Prevention of Delay Graft Function in Cadaveric Kidney Transplants by Calcium Antagonist Diltiazem and Prostacyclin—Analogue Iloorost—Outcome of a Prospective Randomized Clinical Trial,* Transpl. Proc. (in press 1989), Proc. for the Int. Congress Transpl., Sydney, Australia, p.373, 1988), is gaining widespread support. Calcium entry blockers are known to block cell membrane calcium (Ca) channels. This is an important step in the prevention of a cascade of intracellular responses that amplify the post ischemic reperfusion injury. For example, during post ischemic reperfusion, influxes of extracellular Ca cause a sudden increase in cytosolic Ca (Ca$_i$). High levels of Ca$_i$ activates cellular phospholipases, proteinases and will be accumulated in large amounts in mitochondria. By preventing the subsequent Ca dependent enzyme activation of phospholipases (preventing subsequent membrane degradation), xanthine dehydrogenase (XD) activation is also decreased, preventing activation of xanthine oxidase (XO, responsible for the subsequent free radical generation burst during reperfusion). In addition calcium entry blockers can prevent excessive Ca accumulation in mitochondria. Without calcium entry blockers, subsequent high levels of mitochondrial Ca will uncouple oxidative phosphorylation, hence rephosphorylation of ADP to ATP is abolished. As reperfusion progresses, further deterioration of vital cell processes occurs due to inadequate regeneration of ATP, ultimately ending in cell death.

As a result of the recent findings, the present inventors have added various combinations of other additives, such as enzyme inhibitors, free radical scavengers, buffers and calcium entry blockers to their basic PB-2 solution to produce additional flush solutions exhibiting further enhanced preservation properties. In this regard, PB-3 (See Table 2) has demonstrated improved results in enhancing simple hypothermic organ preservation. PB-3 is prepared by mixing allopurinol, verapamil with one liter of PB-2 solution so that the concentrations of allopurinol and verapamil may assume respectively the concentrations set forth in Table 2. In addition, an additional buffer (i.e. KHCO3) is added to increase the pH of the solution to a pH between 7.30 and 7.40. The osmolality of the resulting PB-3 solution remains approximately at 340 mOsm/Kg.

Furthermore, the present invention is also directed to a method for preserving an organ to be transplanted through the use of the adenosine-MgSO4, mannitol intracellular flush and storage solutions described above. Specifically, the organ, such as a kidney, is flushed immediately after its removal from the donor with the adenosine-MgSO4, mannitol intracellular solution of the present invention. The organ is flushed in a sterile storage container until the effluent is clear of blood to achieve rapid cooling and thereby prevent warm ischemic damage. Upon completion of the flushing action, the remainder of the adenosine-MgSO4, mannitol intracellular solution is dispensed into the container which is then sealed and stored on ice in a transportation carton. Alternatively, after initial flushing, the organ can be connected to a preservation machine, such as a MOX-100 preservation machine (Waters Instruments, Inc., Rochester, Minn.) which circulates a cold perfusate through the organ to enable toxic wastes to be removed.

Just prior to transplantation the organ is removed from either the transportation container or the preservation machine, and flushed again with the fluid of the present invention according to the same procedure as outlined above. The organ is then ready for transplantation.

The method and fluid of the present invention improves the condition of the organ transplanted as well as increases the preservation time between donation and transplantation. As a result, the method and fluid of the present invention offers many benefits to society.

The following example further illustrates the specific embodiments of the present invention.

EXAMPLE 1

Materials and Methods

Surgical Procedure

Twenty female mongrel dogs (18–22 kg., USDA approved) were used. An IV hydrating solution of 5.0% dextrose in 0.45% saline at 75 cc/hr was given throughout all procedures. One kidney was exposed by a midline abdominal incision, then removed and flushed with 4° C. PB-2 (Adenosine-Mg SO4, mannitol intracellular cold flush, see Table 2) or C-2 solution.

The animals were divided into two groups and kidneys were flushed with specific cold storage solutions as follows:

Group 1 (N=10) Controls - Kidneys flushed and cold stored with C-2 solution.

Group II (N=10) Kidneys flushed and cold stored with PB-2 solution.

The animals recovered and were fed ad libum. The ex vivo kidneys in both groups were subjected to renal viability analysis by phosphorus-31 magnetic resonance spectroscopy ($^{31}$P-MRS), electron micrographs (EM), and high performance liquid chromatography (HPLC) studies after 50 hours of simple hypothermic storage. Following this initial viability assessment, the animals were re-anesthetized and the midline abdominal incision was reopened.

After contralateral transperitoneal nephrectomy, the preserved kidney was autotransplanted into the right iliac fossa using the iliac artery and vein. An extravesicle ureteroneocystostomy was also constructed. Serial HPLC and EM exams from renal tissue wedge biopsies were performed during the immediate reperfusion period in both groups.

Survival and Renal Function Studies

After transplantation the abdominal incision was closed and the animals were followed for up to 22 days post-transplantation with serial renal function studies, as measured by serum creatinine (measured daily photometrically using an AMES instrument) and the glomerular filtration rate (GFR), determined by clearance calculations of inulin according to the procedure described by Davidson, W. D., Sackner, M. A., *Simplification of Anthrone Method for the Determination of Inulin Clearance Studies*, J. Lab. Clin. Med.; 62:351–356, 1963). GFR measurements were taken as a baseline prior to surgery and after transplantation every 2–4 days, if the animals survived and were stable. Animal survival was recorded as the number of days post-op. At a maximum of 22 days post-transplantation, all animals were sacrificed, and gross and histopathologic examinations of the transplanted kidneys were performed.

HPLC Studies

During (a) normal in-situ, (b) after 50 hours cold storage, (c) after 5 minutes and (d) after 45 minutes of revascularization of the transplanted kidney, renal wedge biopsies were taken from all transplanted kidneys to measure tissue adenine nucleotides, xanthine and hypoxanthine using HPLC. The latter two metabolites are participants in the formation of toxic free radicals.

Freeze-clamped ($-200°$ C.) renal specimens were grinded to a fine powder with a cooled ($-100°$ C.) mortar and pestle. Adenine nucleotides (AN) were extracted from (25–35 mg) portions, using 1 cc of ice cold 2 N perchloric acid with 1 mM EDTA, then neutralized with 1 cc of 2N KHCO3 to pH 6.90±0.10 and centrifuged at 8500 rpm for 4 minutes. 15 ul of resulting supernatant was analyzed by HPLC using a Waters system instrument equipped with a 5 $\mu$m C18 reversed phase column. An isocratic system was applied using 0.3 M NH4PO4 as the mobile phase, titrated with NaOH to pH 6.40. The mobile phase was pumped at 2 ml/min and all separations occurred within 9 minutes. Peak heights were measured at 215 nm and quantitated against external standard (ATP=adeninine triphosphate, ADP-=adenine diphosphate, AMP=adenine monophosphate, HYPO=hypoxanthine, XAN=xanthine) solutions of known concentrations. Total adenine nucleotides (TAN=sum of ATP, ADP and AMP), and degradation products sum (DP=sum of hypoxanthine and xanthine) were calculated from measured concentrations. The frozen specimens were weighed using a hanging balance scale (Mettler Instrument Corp.) and from this the dry tissue weights calculated (0.60 of wet weight). Concentrations were standardized to micromoles/gram dry weight tissue (Belzer, F. O., Downes, G. L.: *Organ Preservation for Transplantation*, Boston, Little, Brown, 1974) (Belzer, F. O. et al.: *A New Perfusate for Kidney Preservation*, Transpl. Proc. 16:161–163, 1984).

$^{31}$P-MRS

Phosphorus-31 MRS of intact canine kidneys were acquired after 50 hours hypothermic storage just prior to autotransplantation. Intracellular phosphorus metabolites were directly monitored by $^{31}$P-MRS in whole canine kidneys using a 2 cm MRS coil placed just external to the cold storage capsule containing the preserved kidney. The midportion of the kidney was centered directly over the coil, enabling monitoring of approximately 10 cc of renal cortex and medulla. Spectra were obtained at 81 MHz on a General Electric CSI-2 spectrometer using a 4.7-Tesla, 40 cm (horizontal bore), superconducting magnet. The H$_2$O signal was used to shim the magnet before acquiring the $^{31}$P spectra.

Signal to noise was optimized using a tip angle of 80 sec. Fourier transforms of 256 acquisitions with a 3 second recycle time were used for measurements. 1024 data points were collected during 64 milliseconds over a spectral width of 4000 Hz, which were Fourier transformed (usually with no line broadening) to 4096 points in the frequency domain. Spectra typically included peaks from intracellular NADP, phosphomonoester (PME), and inorganic phosphate (P$_i$).

The P$_i$ peak observed in these spectra were composed of two components: one arising from intracellular P$_i$ and the other from P$_i$ in the buffer. The latter could be easily identified from an additional spectrum taken under the same conditions, but with the storage container set slightly to the side, so the kidney was off from the center of the surface coil. This peak from the P$_i$ in the buffer could be used as a chemical shift reference. The pH of the buffer medium was measured immediately following the accumulation of the NMR spectra with a Corning Model 140 pH meter. Then the position of the buffer P$_i$ peak was assigned the value calculated from the relation:

$$P_i = 3.22 + 2.51/(1 + 10^{6.803-pH})$$

derived by JP Phasmana et al (Phasmana, J. P., Digerness, S. B., Ng, T. C., Glickson, J. D., Blackstone, E. H., *The Effect of Adenosine Deaminase Inhibitors on the Heart's Functional and Biochemical Recovery From Ischemia*, J. Cardiovasc. Pharmacol. 5: 1040–1047, 1983).

To measure the peak areas of the spectra of the kidneys accurately, they were deconvolved using a multivariant Simplex routine in which the height, width and position of each peak is optimized by a least squares difference criterium. Furthermore, from the position of the intracellular P$_i$ peak, the intracellular pH could be calculated using the inverse of the above equation.

Pre-transplant MRS parameters and the intracellular renal pH were correlated with subsequent renal function in the animals, such as the drop in serum creatinine, inulin renal clearances, and animal survival.

Electron Microscopic Analysis of Variably Ischemic Renal Tissue

A portion of the renal wedge biopsies used for HPLC studies was subjected to EM analysis. Immediately upon removal of selected renal biopsy specimens, 1 mm thick shavings of renal cortex and medulla were dropped in five ml of 0.1 M sodium cacodylate buffer (pH 7.4, at 4C) and 3.75% glutaraldehyde containing 6% sucrose. After 24 hours, the tissue fragments were buffer rinsed and postfixed in cacodylate buffer with 1% osmium tetroxide for one hour, then dehydrated in graded ethanols and embedded in spur resin. Plastic sections (0.1 m) were mounted on glass slides, stained with a mixture of toluidine blue and basic fuchsin then examined by light microscopy. Representative blocks were selected and corresponding thin sections were cut at 60 to 80 nm, stained in uranyl acetate and lead citrate, and examined in a Phillips 400 electron microscope. Endothelial cells and micro-capillary anatomy were examined for evidence of ischemic reperfusion injury.

Statistical Analysis

Categorical data were analyzed using Fisher's Exact Test or Chi-Square depending upon expected cell frequencies. Univariate and multivariate two-way repeated measures ANOVA were utilized as appropriate to access differences due to treatment, time, and treatment by time interaction. After the determination of significant time effects by F-tests, t-tests were conducted to determine specific differences over time. The Statistical Analysis System (Cary, N. C., *SAS User's Guide—Statistics, Version 5 Edition*, SAS Institute Inc., 1965, p. 956) was used to perform all statistical tests. A p value of less than 0.05 was used as the criterion for statistical significance. When used, the results are expressed as the mean ±S.D.

Results

Recovery of Renal Function and Survival

All autorenal transplants were technically successful with no vascular or urologic complications noted on autopsy. Deaths from pneumonia occurred randomly for each group and these were excluded from statistical analysis of survival (Table 3) (PB-2: n=4, C-2: n=3). While immediate reperfusion and firmness was noted in all kidneys after revascularization, the C-2 group had a palpable decrease in firmness after 45 minutes.

TABLE 3

| COMPARISON OF PRESERVATION SOLUTIONS BY SURVIVAL POST AUTORENAL TRANSPLANTATION | | | |
|---|---|---|---|
| Survival | | PB-2 | C-2 |
| # of Animals Surviving | > 7 days | 8/10  p < 0.01 | 3/10 |
| | > 14 days | 4/10  P < 0.01 | 1/10 |
| Days Survival Post Transplant* | | 22 | 6 |
| | | 15 | 2 |
| | | 15 | 6 |
| | | 8 | 15 |
| | | | 4 |
| | | 15 | 5 |
| | | 8 | 6 |
| | | 14 ± 5 | 6 ± 4 |
| | | p < 0.02 | |

Animal survival was significantly greater in the PB-2 group as seen by the number of animals surviving 7 days and 14 days (p<0.01), as well as the mean number of days post renal transplantation (p<0.02) (Table 3).

The variable survival and condition of the animals post transplantation limited complete monitoring of serum creatinine (Table 4) and inulin clearance (Table 5) for all animals. Nevertheless, both measurements reflected superior renal function recovery in the PB-2 group, compared to the C-2 group.

TABLE 4

| POST TRANSPLANT MEAN SERUM CREATININES (mg/dl) | | | | | | | | |
|---|---|---|---|---|---|---|---|---|
| Days Post Op | 0 | 1 | 2 | 3 | 4 | 5 | 6 | 7 |
| PB-2 | 1.00 | 5.37 | 6.89 | 8.44 | 8.40 | 7.87 | 6.40 | 2.88 |

TABLE 4-continued

| | POST TRANSPLANT MEAN SERUM CREATININES (mg/dl) | | | | | | | |
|---|---|---|---|---|---|---|---|---|
| Days Post Op | 0 | 1 | 2 | 3 | 4 | 5 | 6 | 7 |
| C-2 | 1.17 | 5.96 | 8.37 | 10.38 | 11.13 | 13.35 | 12.33 | 12.18 |

TABLE 5

| | POST-TRANSPLANT INULIN CLEARANCE (ml/min) | | |
|---|---|---|---|
| | PRE-OP | | POST-OP |
| PB-2 | 37.6 ± 6.2 | NS | 42.9 ± 33.8 |
| C-2 | 51.3 ± 15.6 | p < 0.001 | 14.6 ± 16.0 |

Figure 3:
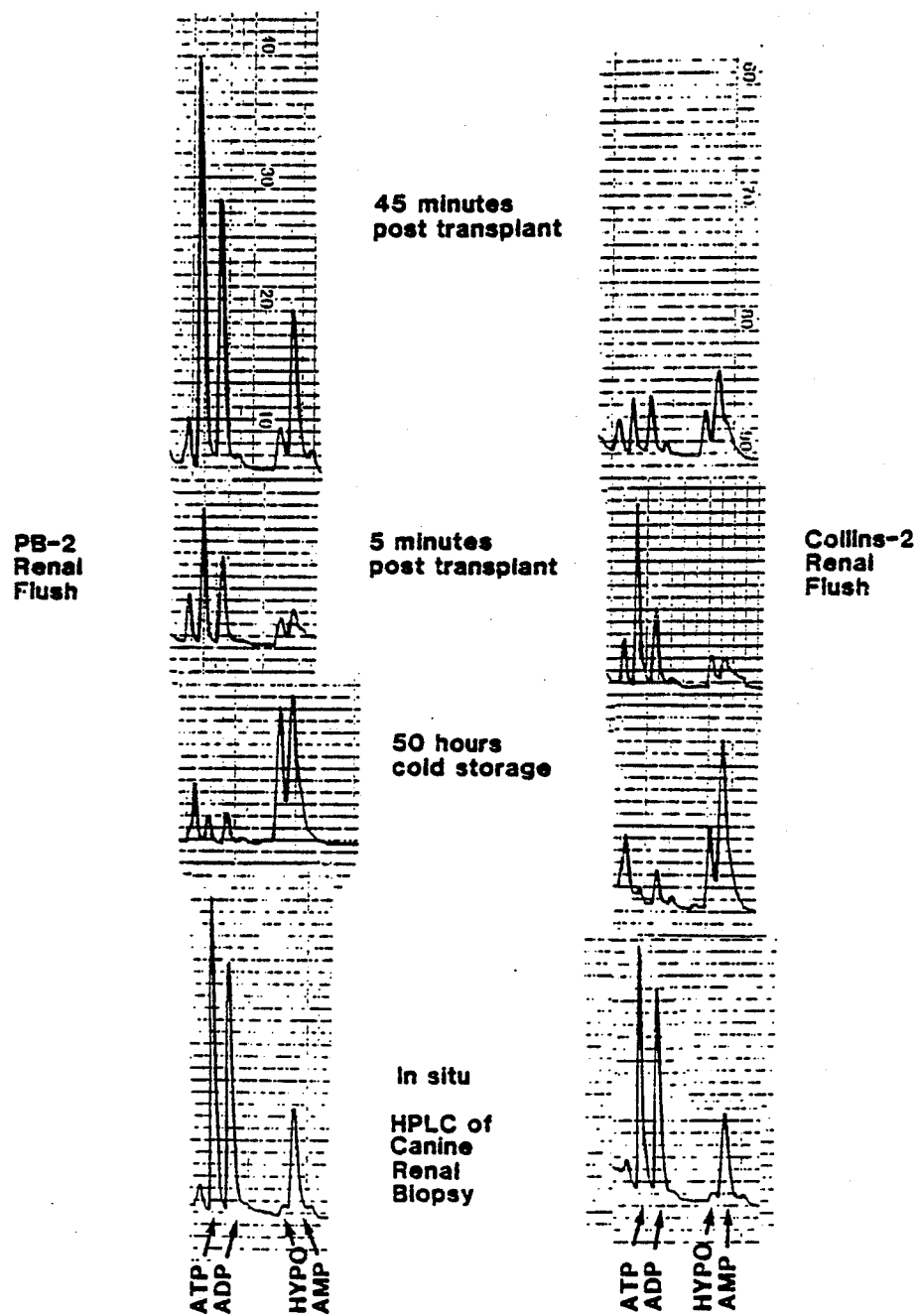
FIG. 3 is a reproduction of the results of high performance liquid chromatography (HPLC) of canine renal biopsies of the PB-2 renal flush and the Collins' C-2 renal flush.

HPLC Studies Total Adenine Nucleotides (TAN) and adenine monophosphate (AMP) were significantly higher after 50 hours of cold storage in the PB-2 group compared with the C-2 group (4.60±1.47 vs. 3.32±1.50 mole/gram dry weight tissue, p<0.01 and 3.30±0.97 vs. 2.42±0.67 moles/gram dry weight tissue, p<0.03). TAN were significantly (p<0.03) higher and degradation products (DP) significantly (p<0.05) lower (despite having had significantly (p<0.001) higher levels after cold storage) in the PB-2 group after 45 minutes of reperfusion compared to the C-2 group (Table 6). FIG. 3 demonstrates a typical comparison of the regeneration of AMP, ADP and ATP by PB-2 compared to C-2. While no significant difference was noted at five minutes of reperfusion, a difference was observed by 45 minutes. Further deterioration of TAN noted during the interval between five and 45 minutes within the C-2 group is consistent with post-reperfusion injury.

TABLE 6

| HPLC OF CANINE RENAL BIOPSIES | | | |
|---|---|---|---|
| TAN[a]: | PB-2[c] | C-2 | p-value |
| In situ | 6.54 ± 2.33 | 5.32 ± 1.50 | NS |
| 50 hours cold storage | 4.60 ± 1.47 | 3.32 ± 1.50 | p = 0.01 |
| Five minutes reperfusion | 3.08 ± 0.98 | 3.01 ± 1.53 | NS |
| 45 minutes reperfusion | 4.87 ± 2.10 | 3.08 ± 0.99 | p = 0.02 |
| In situ | 0.21 ± 0.11 | 0.31 ± 0.32 | NS |
| 50 hours cold storage | 3.06 ± 1.19 | 1.01 ± 0.78 | p < 0.001 |
| Five minutes reperfusion | 0.27 ± 0.21 | 0.23 ± 0.08 | NS |
| 45 minutes reperfusion | 0.25 ± 0.19 | 0.41 ± 0.16 | p < 0.05 |

[a]-TAN (Total Adenine Nucleotides) = ATP + ADP + AMP.
[b]-DP (Degradation Products) = hypoxanthine + xanthine
[c]-All levels reported as #moles/gram dry wt. renal cortical tissue

$^{31}$P-MRS Studies

Figure 4A:
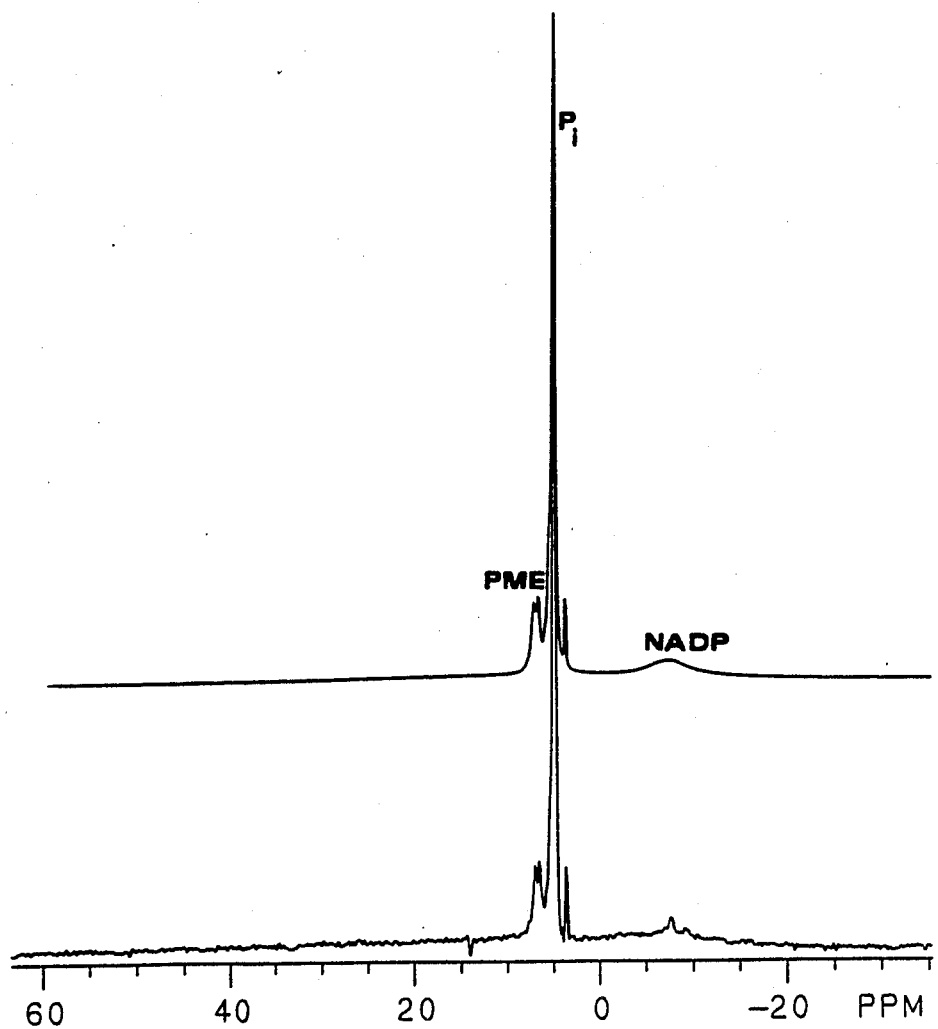
FIGS. 4a and 4b are representative phosphorus-31 magnetic resonance spectroscopy ($^{31}$P-MRS) spectras from whole canine kidneys at 50 hours cold storage just prior to transplantation of the PB-2 embodiment of the present invention (FIG. 4a) and the Collins' C-2 (FIG. 4b) solution.
Figure 4B:
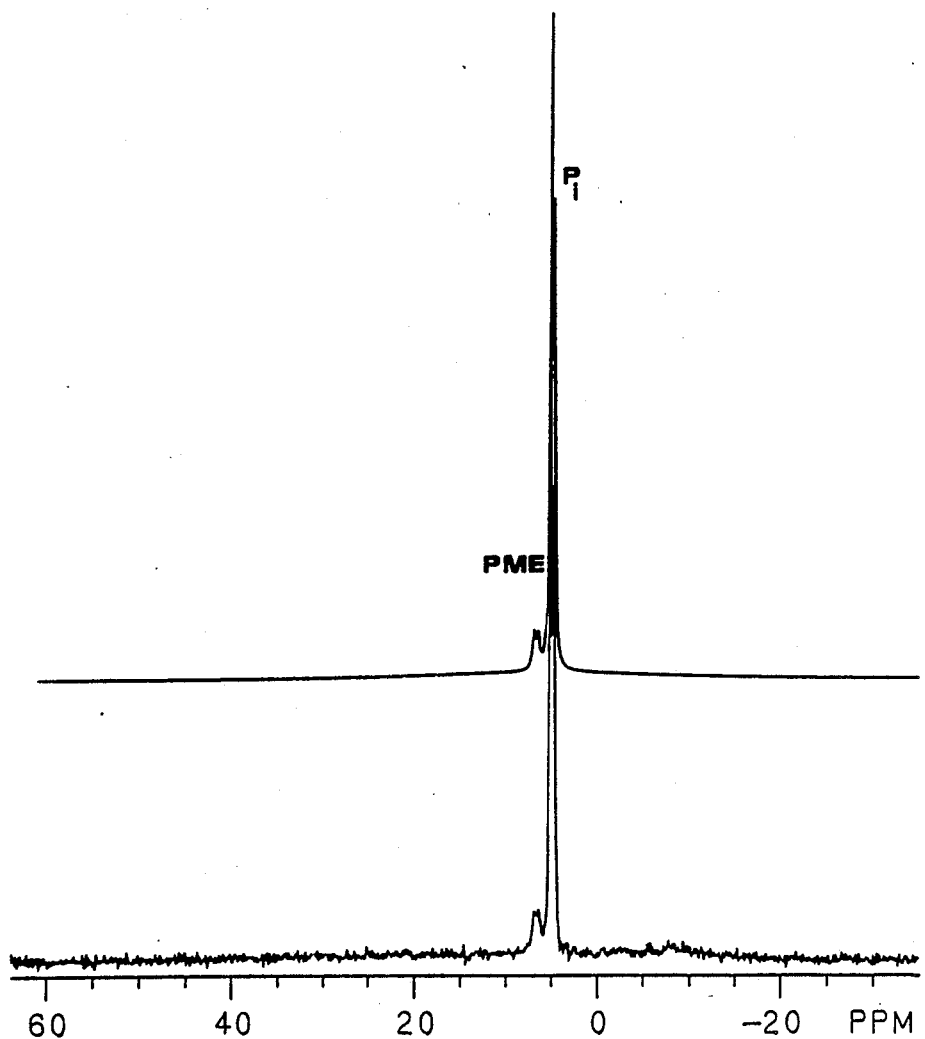

High energy phosphorus metabolites were higher in the (PME/P$_i$: 0.41±0.26 vs. 0.26±0.09, p<0.10 and NADP/P$_i$:0.36±0.41 vs. 0.01±0.03, p<0.0001) PB-2 group compared to C-2 group just prior to transplantation, however no significant difference in intracellular pH was noted (7.13 vs. 7.20, NS). Representative spectra illustrate these major differences of renal intracellular metabolites (FIG. 4A and 4B).

EM Studies

Figure 5:
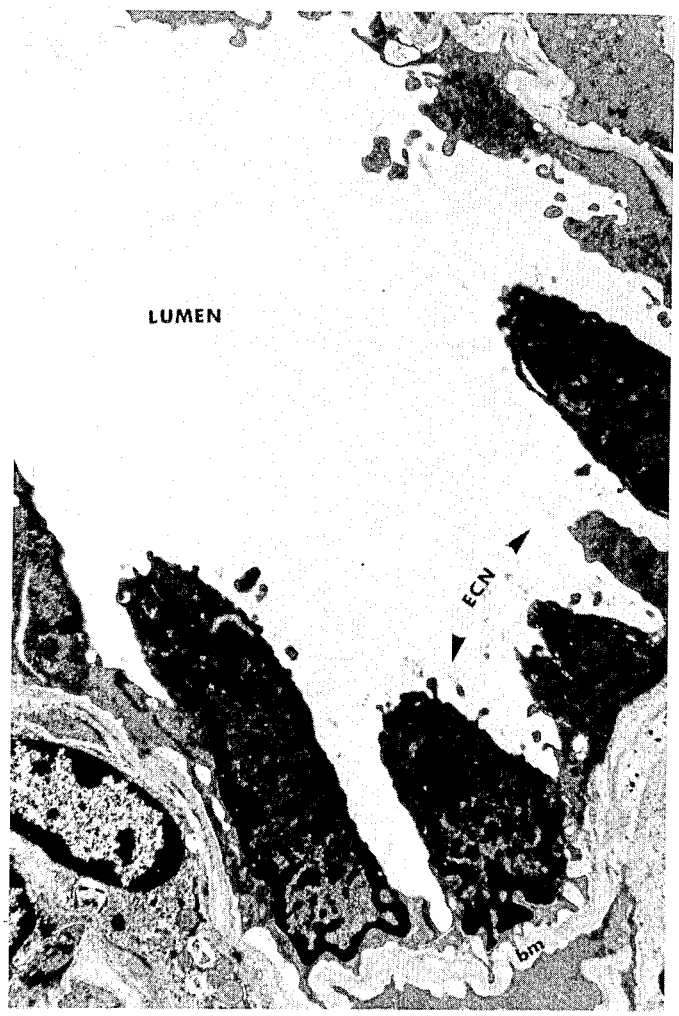
FIG. 5 is an electron photomicrograph of a normal canine biopsy from kidneys flushed and stored with the PB-2 embodiment of the present invention for 50 hours, then reperfused for 45 minutes; (the magnification of FIG. 5 is 10,320×); and, FIGS. 6a, 6b, 6c, and 6d are electron photomicrographs of a post 45 minute reperfusion biopsy of 50 hours cold stored Collins' C-2 flush canine kidneys. (The magnification of the respective FIGURES is 6,960×).
Figure 6A:
Figure 6B:
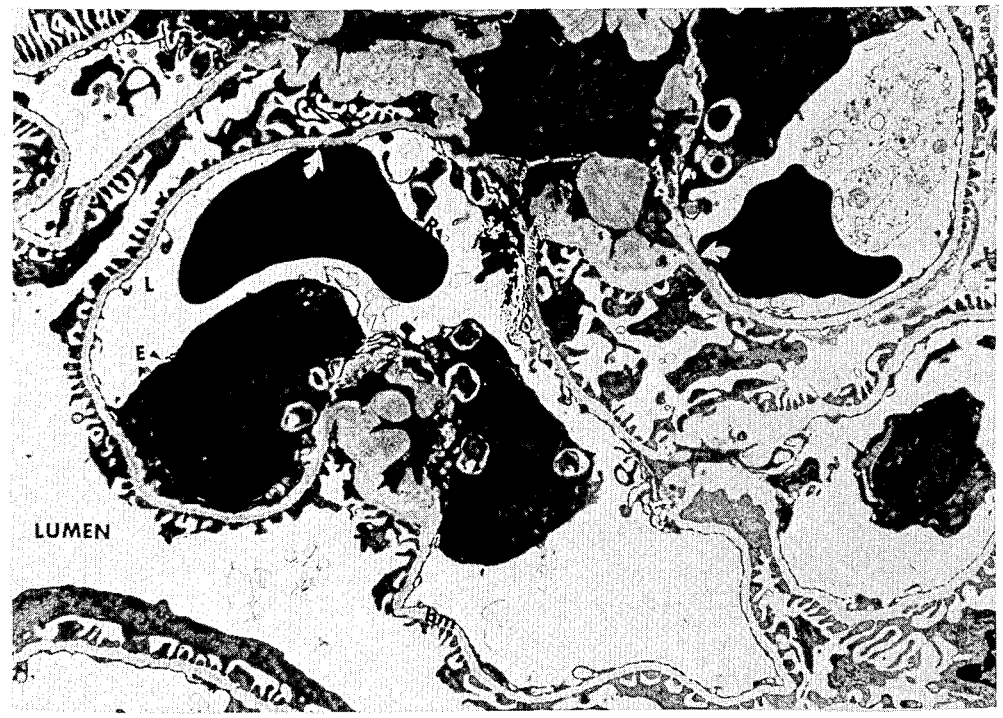
Figure 6C:
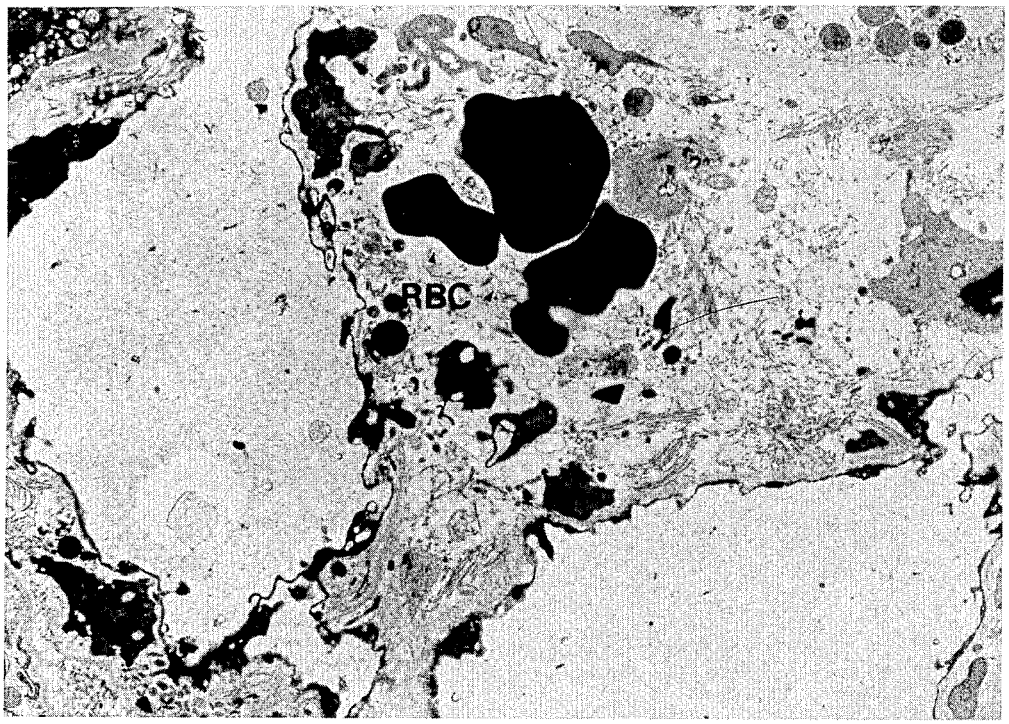
Figure 6D:
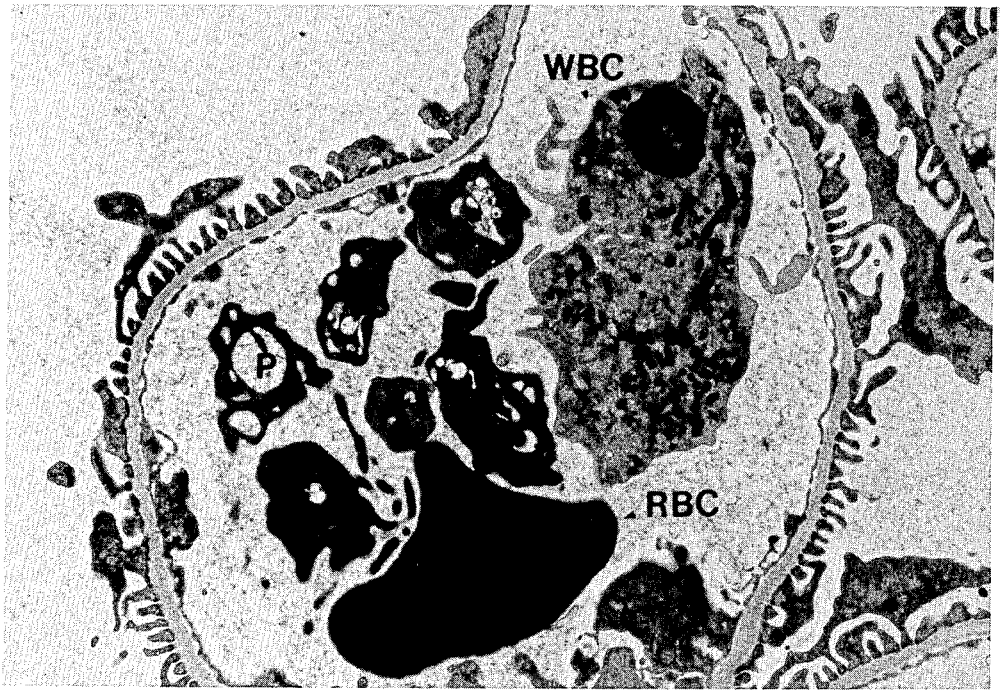

EM analysis revealed normal endothelial cell (ECN) morphology and patent micro-capillary lumens from control in situ biopsies of normal kidneys in both the PB-2 and C-2 groups. However, while PB-2 flushed kidneys at five minutes (FIG. 5) and at 45 minutes post reperfusion were also normal, the biopsies from C-2 flushed kidneys at these intervals were associated with red blood cell (RBC) clumping within the microcapillary lumen via RBC-RBC (FIG. 6A) and RBC-ECN (FIG. 6B) adhesiveness. In addition, interstitial microhemorrhage (FIG. 6C) and aggregation of leucocytes (WBCs), RBCs and platelets within the capillary lumen were frequently noted (FIG. 6D). These changes were progressive during the five to 45 minute reperfusion period.

DISCUSSION

HLPC Results

Recent studies using HPLc (Maessen, J. G., van der Vusse, G. J., Vork, M., et al., *Determination of Warm Ischemia Time at Donor Nephrectomy*, Transpl. 45:147–152, 1988), $^{31}$P-MRS (Claes, G., et al.: *Albumin as Perfusate in Continuous Perfusion for Renal Preservation*, Fourth International Transplant conference, New York, Grune and Stratton, p. 46, 1972); and, (Collins, G. M., Halasz, N. A.: *Forty-eight Hour Ice Storage of Kidneys Importance of Cation Content*, Surg. 79:432–435, 1976) and EM (Neil, D., Pollock, G. A., Molyneux, G. S., Hardie, I. R., *Vascular Changes Following Hypothermic Perfusion*, Transpl. Proc. (in press) 1989) have helped elucidate cellular processes integral to successful preservation. Higher AMP levels, as demonstrated by HPLC, correspond directly with higher levels of PME, as measured by MRS at 50 hours of cold storage. These findings are consistent with other recent observations showing that the PME peak may be predominately composed of AMP (Baldwin, N., Bretan, P. N., Scarpa, A., *Predominance of Renal Phosphomonoester (PME)* $^3$P-MRS *Peak by AMP-Correlative and Quantitative Analysis Using HPLC Assay*, Proceeding of Society of Magnetic Resonance in Medicine (Works in Progress Suppl), p. 77, 1988). HPLC and $^{31}$P-MRS are demonstrated to be complimentary methods which can identify different intracellular metabolites that are necessary for tissue viability.

The higher HPLC measured levels of DP at 50 hours of cold storage, should predict a more severe reperfusion injury, since DP are associated with the formation of toxic free radicals. However, this was not observed (Table 4), possibly reflecting the efficiency of mannitol (a free radical scavenger) in PB-2 solution to minimize this effect.

$^{31}$P-MRS Results

In the present study, $^{31}$P-MRS 50 hour cold storage measurements, just prior to renal transplantation, revealed greater levels of PME (predominately AMP, p<0.10) and NADP (p<0.001). No correlation with intracellular renal pH and subsequent viability was noted. These findings are consistent with recent observations in human kidneys studied by MRS demonstrating the ability of this method to assess renal viability accurately (Bretan, P. N., Baldwin, N., Novick, A. C., et al., *Preliminary Clinical Experience With Pretransplant Assessment of Renal Viability by* $^{31}$P-MRS, Transpl. Proc., 20: 852, 1988) during cold storage. In addition the current study shows that greater preservation of high energy intracellular phosphorus metabolites occurs with PB-2 compared to C-2. This mechanism may be completely separate from those which alleviate reperfusion injury, and the use of adenosine within PB-2 may account for this by retarding ischemic catabolism of AMP and adenosine (FIG. 2) through inhibition of the responsible enzymes.

EM Results

Figure 2:
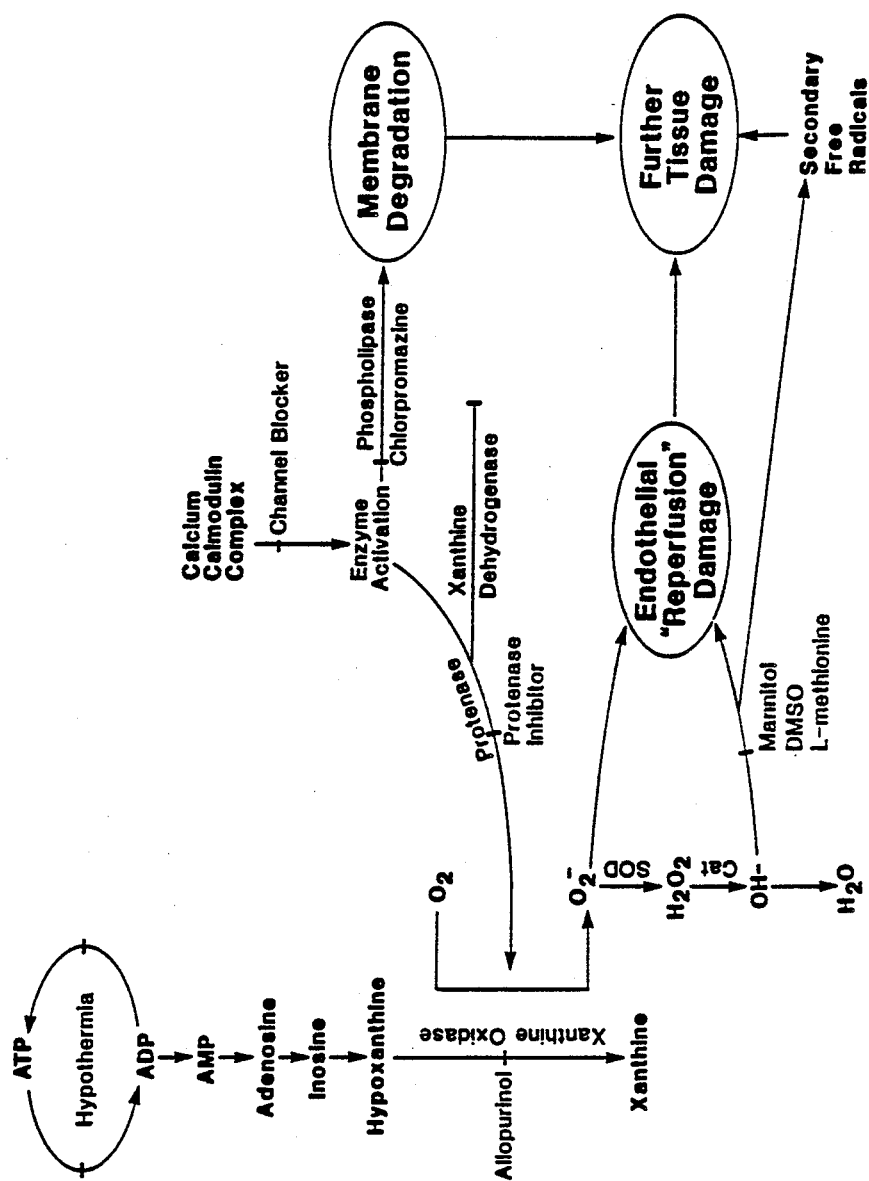
FIG. 2 is a schematic diagram illustrating the ischemic renal metabolic pathways involved in renal transplant preservation.

The current EM studies further define morphologic criteria for reperfusion injury following cold preservation. We noted an increase in RBC, WBC and platelet aggregation in the microcapillaries of the kidney. This occurrence has been supported by studies using $^{51}$Cr-labelled erythrocytes. For example, Jacobsson and co-workers (Jacobsson, J., Odlind, B., Tufveson, G., Wahlberg, J., *Effects of Cold Ischemia and Reperfusion on the Trapping of Erythrocytes in the Rat Kidney*, Transpl. Int. 1:75–79, 1988) have shown that reperfusion following cold ischemia in the rat kidney causes a significant increase in RBC trapping. This effect may be prevented with the use of free radical scavengers (FRS), such as superoxide dismutase or allopurinol. Thus, the reperfusion injury appears to be mediated by oxygen-derived free radicals (FR), such as superoxide ($O_{-2}$) and hydroxyl ion ($OH^-$) (FIG. 1). These FR can disrupt cell membranes, resulting in severe vascular endothelial cell damage during the reperfusion period, contributing to further surrounding tissue damage (FIGS. 1 & 2). During cold storage, ischemia causes extensive ATP and other ANs catabolism resulting in accumulation of tissue hypoxanthine (FIG. 2). The latter is a substrate for xanthine oxidase, which generates high levels of FR during reperfusion. Extensive ATP catabolism from ischemia in itself is a major component of irreversible tissue injury. The ischemic (catabolic derived) and reperfusion (FR derived) components are the two major contributors to total post ischemic renal injury as supported by recent studies of Hoshino and co-workers (Hoshino T., Maley, W. R., Bulkley, G. B., Williams, G. M., *Ablation of Free Radical-Mediated Reperfusion Injury for the Salvage of Kidneys Take From Non-heart Beating Donors—a Quantitative Evaluation of the Proportion of Injury Caused by Reperfusion Following Periods of Warm, Cold, and Combined Ischemia*, Transpl. 45:284–289, 1988). Both of these mechanisms must be adequately controlled in order for enhancement of renal preservation.

The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims and the equivalents thereof.

Having thus described the preferred embodiments, the invention is now claimed to be:

1. An intracellular flush solution for preserving an organ for transplantation, comprising:
   (a) between about 1.54 and 2.56 grams per liter of $KH_2PO_4$;
   (b) between about 7.38 and 12.2 grams per liter of $K_2HPO_4$;
   (c) between about 0.84 and 1.40 grams per liter of KCl;
   (d) between about 0.63 and 1.05 grams per liter of $NaHCO_3$;
   (e) between about 0 and 2.87 grams per liter of $KHCO_3$;
   (f) between about 20 and 37 grams per liter of mannitol;
   (g) between about 0 and 4.62 grams per liter of $MgSO_4$;
   (h) between about 0 and 0.4 meq/ml of $MgCl_2$;
   (i) between about 0.75 and 1.25 grams per liter of adenosine;
   (j) between about 0 and 0.125 grams per liter of allopurinol; and,
   (k) between about 0 and 1.0 grams per liter of verapamil.

2. The intracellular flush solution of claim 1, wherein said mannitol is present in an amount sufficient to adjust the osmolality of the solution to a value between about 255 and 425 mOsm/Kg.

3. An intracellular flush solution for preserving an organ for transplantation, comprising:
   (a) between about 1.54 and 2.56 grams per liter of $KH_2PO_4$;
   (b) between about 7.38 and 12.2 grams per liter of $K_2HPO_4$;
   (c) between about 0.84 and 1.40 grams per liter of KCl;
   (d) between about 0.63 and 1.05 grams per liter of $NaHCO_3$;
   (e) between about 0 and 2.87 grams per liter of $KHCO_3$;
   (f) between about 20 and 37 grams per liter of mannitol;
   (g) between about 0.2 and 0.4 meq/ml of $MgCl_2$;
   (h) between about 0.75 and 1.25 grams per liter of adenosine;
   (i) between about 0 and 0.125 grams per liter of allopurinol; and,
   (j) between about 0 and 1.0 grams per liter of verapamil.

4. An intracellular flush solution for preserving an organ for transplantation comprising: about 2.05 grams per liter $KH_2PO_4$; about 9.7 grams per liter $K_2HPO_4$; about 1.12 grams per liter KCl; about 0.84 grams per liter $NaHCO_3$; about 25.0 grams per liter mannitol; about 3.7 grams per liter $MgSO_4$; and about 1.0 grams per liter adenosine.

5. An intracellular flush solution for preserving an organ for transplantation comprising: about 2.05 grams per liter $KH_2PO_4$; about 9.7 grams per liter $K_2HPO_4$; about 1.12 grams per liter KCl; about 0.84 grams per liter $NaHCO_3$; about 2.3 grams per liter $KHCO_3$; about 25.0 grams per liter mannitol; about 3.7 grams per liter $MgSO_4$; about 1.0 grams per liter adenosine; about 0.1 grams per liter allopurinol; and, about 0.007 verapamil.

6. An intracellular flush solution for preserving an organ for transplantation comprising:
   (a) a modified Collins C-2 solution containing about 2.05 grams per liter of $KH_2PO_4$; about 9.70 grams per liter $K_2HPO_4$, about 1.12 grams per liter KCl; and, about 0.84 grams per liter $NaHCO_3$;
   (b) about 25 grams per liter mannitol;
   (c) about 3.7 grams per liter $MgSO_4$; and,
   (d) about 1.0 grams per liter adenosine.

7. An intracellular flush solution for preserving an organ for transplantation comprising:
   (a) a modified Collins C-2 solution containing about 2.05 grams per liter of $KH_2PO_4$; about 9.70 grams per liter $K_2HPO_4$, about 1.12 grams per liter KCl; and, about 0.84 grams per liter $NaHCO_3$;
   (b) about 25 grams per liter mannitol;
   (c) about 3.7 grams per liter $MgSO_4$;

(d) about 1.0 grams per liter adenosine;
(e) about 2.3 grams per liter KHCO$_3$;
(f) about 0.1 grams per liter allopurinol; and,
(g) about 0.007 grams per liter verapamil.

8. An intracellular flush solution for preserving an organ for transplantation comprising a modified Collins C-2 solution devoid of glucose and MgSO$_4$; and, about 25 grams per liter mannitol; about 3.7 grams per liter MgSO$_4$; and about 1.0 grams per liter adenosine.

9. An intracellular flush solution for preserving an organ for transplantation comprising a modified Collins C-2 solution devoid of glucose and MgSO$_4$; and, about 25 grams per liter mannitol; about 3.7 grams per liter MgSO$_4$; about 1.0 grams per liter adenosine; about 2.3 grams per liter KHCO$_3$; about 0.1 grams per liter allopurinol; and, about 0.007 grams per liter verapamil.

10. A method for preserving an organ for transplantation comprising flushing the organ to be transplanted with an intracellular flush solution comprising:
    (a) between about 1.54 and 2.56 grams per liter of KH$_2$PO$_4$;
    (b) between about 7.38 and 12.2 grams per liter of K$_2$HPO$_4$;
    (c) between about 0.84 and 1.40 grams per liter of KCl;
    (d) between about 0.63 and 1.05 grams per liter of NaHCO$_3$;
    (e) between about 0 and 2.87 grams per liter of KHCO$_3$;
    (f) between about 20 and 37 grams per liter of mannitol;
    (g) between about 2.77 and 4.62 grams per liter of MgSO$_4$;
    (h) between about 0.75 and 1.25 grams per liter of adenosine;
    (i) between about 0 and 0.125 grams per liter of allopurinol; and,
    (j) between about 0 and 1.0 grams per liter of verapamil.

11. A method for preserving an organ for transplantation comprising flushing the organ to be transplanted with an intracellular flush solution comprising:
    (a) between about 1.54 and 2.56 grams per liter of KH$_2$PO$_4$;
    (b) between about 7.38 and 12.2 grams per liter of K$_2$HPO$_4$;
    (c) between about 0.84 and 1.40 grams per liter of KCl;
    (d) between about 0.63 and 1.05 grams per liter of NaHCO$_3$;
    (e) between about 0 and 2.87 grams per liter of KHCO$_3$;
    (f) between about 20 and 37 grams per liter of mannitol;
    (g) between about 0.2 and 0.4 meq/ml of MgCl$_2$;
    (h) between about 0.75 and 1.25 grams per liter of adenosine;
    (i) between about 0 and 0.125 grams per liter of allopurinol; and,
    (j) between about 0 and 1.0 grams per liter of verapamil.

12. A method for preserving an organ for transplantation comprising flushing the organ to be transplanted with an intracellular flush solution comprising about 2.05 grams per liter KH$_2$PO$_4$; about 9.7 grams per liter K$_2$HPO$_4$; about 1.12 grams per liter KCl; about 0.84 grams per liter NaHCO$_3$; about 25.0 grams per liter mannitol; about 3.7 grams per liter MgSO$_4$; and about 1.0 grams per liter adenosine.

13. A method for preserving an organ for transplantation comprising flushing the organ to be transplanted with an intracellular flush solution comprising about 2.05 grams per liter KH$_2$PO$_4$; about 9.7 grams per liter K$_2$HPO$_4$; about 1.12 grams per liter KCl; about 0.84 grams per liter NaHCO$_3$; about 2.3 grams per liter KHCO$_3$; about 25.0 grams per liter mannitol; about 3.7 grams per liter MgSO$_4$; about 1.0 grams per liter adenosine; about 0.1 grams per liter allopurinol; and, about 0.007 verapamil.

14. A method for preserving an organ for transplantation comprising flushing the organ to be transplanted with an intracellular flush solution comprising:
    (a) a modified Collins C-2 solution containing about 2.05 grams per liter of KH$_2$PO$_4$; about 9.70 grams per liter K$_2$HPO$_4$, about 1.12 grams per liter KCl; and, about 0.84 grams per liter NaHCO$_3$;
    (b) about 25 grams per liter mannitol;
    (c) about 3.7 grams per liter MgSO$_4$; and,
    (d) about 1.0 grams per liter adenosine.

15. A method for preserving an organ for transplantation comprising flushing the organ to be transplanted with an intracellular flush solution comprising:
    (a) a modified Collins C-2 solution containing about 2.05 grams per liter of KH$_2$PO$_4$; about 9.70 grams per liter K$_2$HPO$_4$, about 1.12 grams per liter KCl; and, about 0.84 grams per liter NaHCO$_3$;
    (b) about 25 grams per liter mannitol;
    (c) about 3.7 grams per liter MgSO$_4$;
    (d) about 1.0 grams per liter adenosine;
    (e) about 2.3 grams per liter KHCO$_3$;
    (f) about 0.1 grams per liter allopurinol; and,
    (g) about 0.007 grams per liter verapamil.

16. A method for preserving an organ for transplantation comprising flushing the organ to be transplanted with an intracellular flush solution comprising a modified Collins' C-2 solution devoid of glucose and MgSO$_4$; and, about 25 grams per liter mannitol; about 3.7 grams per liter MgSO$_4$; and about 1.0 grams per liter adenosine.

17. A method for preserving an organ for transplantation comprising flushing the organ to be transplanted with an intracellular flush solution comprising a modified Collins C-2 solution devoid of glucose and MgSO$_4$; and, about 25 grams per liter mannitol; about 3.7 grams per liter MgSO$_4$; about 1.0 grams per liter adenosine; about 2.3 grams per liter KHCO$_3$; about 0.1 grams per liter allopurinol; and, about 0.007 grams per liter verapamil.

* * * * *